US008883442B2

(12) United States Patent
Martinez et al.

(10) Patent No.: US 8,883,442 B2
(45) Date of Patent: Nov. 11, 2014

(54) CULTURE MEDIUM, METHOD FOR CULTURING *LISTERIA*, AND METHOD FOR DETECTING *LISTERIA*

(75) Inventors: Gabriela Martinez, St. Hyacinthe (CA); David Claveau, Farnham (CA); Lila Maduro, St. Hyacinthe (CA)

(73) Assignee: Foodchek Systems, Inc., Calgary (CA)

( * ) Notice: Subject to any disclaimer, the term of this patent is extended or adjusted under 35 U.S.C. 154(b) by 0 days.

(21) Appl. No.: 13/546,665

(22) Filed: Jul. 11, 2012

(65) Prior Publication Data

US 2013/0017569 A1 Jan. 17, 2013

Related U.S. Application Data

(60) Provisional application No. 61/507,193, filed on Jul. 13, 2011.

(51) Int. Cl.
*C12N 9/08* (2006.01)
*C12N 9/02* (2006.01)
*C12N 1/20* (2006.01)
*C12Q 1/04* (2006.01)
*C12N 1/00* (2006.01)
*C12Q 1/02* (2006.01)
*C12Q 1/00* (2006.01)

(52) U.S. Cl.
CPC . *C12Q 1/045* (2013.01); *C12N 1/20* (2013.01)
USPC .......... 435/34; 435/253.6; 435/192; 435/189; 435/252.1; 435/4; 435/243

(58) Field of Classification Search
None
See application file for complete search history.

(56) References Cited

U.S. PATENT DOCUMENTS

| | | | |
|---|---|---|---|
| 5,145,786 A * | 9/1992 | Bailey et al. | 435/252.4 |
| 5,296,370 A | 3/1994 | Martin et al. | |
| 5,391,495 A | 2/1995 | Patel et al. | |
| 5,573,947 A | 11/1996 | Madec et al. | |
| 5,633,162 A | 5/1997 | Keen et al. | |
| 5,658,790 A | 8/1997 | Gautsch | |
| 5,861,270 A | 1/1999 | Nelis | |
| 5,925,550 A | 7/1999 | Lancini et al. | |
| 5,962,306 A | 10/1999 | Ollar et al. | |
| 6,019,984 A | 2/2000 | MacInnes et al. | |
| 6,165,776 A | 12/2000 | Eklund et al. | |
| 6,197,574 B1 | 3/2001 | Miyamoto et al. | |
| 6,261,803 B1 | 7/2001 | Zander et al. | |
| 6,558,917 B2 | 5/2003 | Schabert | |
| 6,846,664 B2 | 1/2005 | Dash et al. | |
| 6,984,406 B2 | 1/2006 | Cho et al. | |
| 7,351,548 B2 | 4/2008 | Rambach | |
| 7,407,775 B2 | 8/2008 | Roger-Dalbert et al. | |
| 7,449,311 B2 | 11/2008 | De Vuyst et al. | |
| 7,484,560 B2 | 2/2009 | Lal et al. | |
| 7,618,805 B2 | 11/2009 | Horn | |
| 7,642,060 B2 * | 1/2010 | Nagar et al. | 435/7.2 |
| 7,655,454 B1 | 2/2010 | Hinton | |
| 7,771,964 B2 | 8/2010 | Kim et al. | |
| 7,960,164 B2 | 6/2011 | Olstein | |
| 8,501,457 B2 | 8/2013 | Li et al. | |
| 8,518,688 B1 | 8/2013 | Peterson et al. | |
| 2004/0121445 A1 | 6/2004 | Marino et al. | |
| 2011/0065145 A1 | 3/2011 | Fovet et al. | |
| 2011/0097784 A1 | 4/2011 | Rahman et al. | |
| 2011/0159515 A1 | 6/2011 | Stimson | |
| 2011/0189733 A1 | 8/2011 | Niphadkar et al. | |
| 2012/0045836 A1 | 2/2012 | Neubauer et al. | |
| 2012/0052492 A1 | 3/2012 | Li | |
| 2012/0052493 A1 | 3/2012 | Li | |
| 2012/0052495 A1 | 3/2012 | Li | |
| 2012/0237497 A1 | 9/2012 | Wegman | |
| 2013/0149739 A1 | 6/2013 | Fovet | |

FOREIGN PATENT DOCUMENTS

| | | | |
|---|---|---|---|
| CA | 2634325 | A1 | 6/2007 |
| CA | 2660147 | A1 | 2/2008 |
| WO | 2011/018472 | A2 | 2/2011 |
| WO | 2012/110435 | A1 | 8/2012 |
| WO | 2012/110960 | A2 | 8/2012 |
| WO | 2013/088448 | A1 | 6/2013 |
| WO | 2013/137622 | A1 | 9/2013 |

OTHER PUBLICATIONS

Atlas, Ronald M; "The Handbook of Microbiological Media for the Examination of Food," CRC Press, 2006.*

Mendonca, A., F. and Knabel, S., J. 1994. A novel strictly anaerobic recovery and enrichment system incorporating lithium for detection of heat-injured *Listeria monocytogenes* in pasteurized milk containing background microflora. Appl. Environ. Microbiol. 60: 4001-4008.

Beumer R. R., te Giffel M. C., Anthonie S. V. R., Cox L. J. 1996. The effect of acriflavine and nalidixic acid on the growth of *Listeria* spp. in enrichment media. F. Microbiol. 13 (2): 137-148.

Teo, A., Y-L., Knabel, S., J. 2000. Development of a Simple Recovery-Enrichment System for Enhanced Detection of Heat-Injured *Listeria monocytogenes* in Pasteurized Milk. J. Food Prot. 63 (4): 462-472.

Busch SV, Donnelly CW. Development of a repair-enrichment broth for resuscitation of heat-injured *Listeria monocytogenes* and *Listeria innocua*. 1992. Appl. Environ. Microbiol. 58(1):14-20.

Buchrieser C, Rocourt J. 2007. The genus *Listeria* and *Listeria monocytogenes*: phylogenetic position, taxonomy, and identification. In: *Listeria*, listeriosis, and food safety, 3rd edition. / Ed. by Ryser ET, Marth EH. CRC Press. 896 p.

(Continued)

Primary Examiner — Blaine Lankford
Assistant Examiner — David Berke-Schlessel
(74) Attorney, Agent, or Firm — Kilpatrick Townsend & Stockton LLP

(57) ABSTRACT

There are disclosed a culture media and culture supplements for cultivating microorganisms, including *Listeria* spp and methods for culturing microorganisms including *Listeria* spp. There are also disclosed methods for detecting the presence of microorganisms including *Listeria* spp in samples.

15 Claims, No Drawings

(56) References Cited

OTHER PUBLICATIONS

Lang Halter E, Neuhaus K, Scherer S. 2012. *Listeria weihenstephanensis* sp. nov., isolated from the water plant *Lemna trisulca* of a German fresh water pond. Int J Syst Evol Microbiol. Apr 27. [Epub ahead of print].

Bertsch D, Rau J, Eugter MR, Haug MC, Lawson PA, Lacroix C, Meile L. 2012. *Listeria fleischmannii* sp. nov., isolated from cheese. Int J Syst Evol Microbiol. Apr 20. [Epub ahead of print].

Painter J, Slutsker L. Listeriosis in humans. 2007. The genus *Listeria* and *Listeria monocytogenes*: phylogenetic position, taxonomy, and identification. In: *Listeria*, listeriosis, and food safety, 3rd edition. / Ed. by Ryser ET, Marth EH. CRC Press. 896 p.

Wesley IV. Listeriosis in animals. 2007. The genus *Listeria* and *Listeria monocytogenes*: phylogenetic position, taxonomy, and identification. In: *Listeria*, listeriosis, and food safety, 3rd edition. / Ed. by Ryser ET, Marth EH. CRC Press. 896 p.

Ramaswamy V, Cresence VM, Rejitha JS, Lekshmi MU, Dharsana KS, Prasad SP, Vijila HM. 2007. *Listeria*—review of epidemiology and pathogenesis. J Microbiol Immunol Infect. 40 (1): 4-13.

Koch J, Stark K. Significant increase of listeriosis in Germany—epidemiological patterns 2001-2005. (2006). Euro Surveill. 11 (6): 85-8.

Anonymous. Incidence of Foodborne Illness, 2010. (http://www.cdc.gov/Features/dsFoodborneIllness/).

EU summary report on trends and sources of zoonoses and zoonotic agents and food-borne outbreaks 2009. (http://www.efsa.europa.eu/en/efsajournal/doc/2090.pdf).

Scallan E, Hoekstra RM, Angulo FJ, Tauxe RV, Widdowson M-A, Roy SL, Jones JL, Griffin PM. Foodborne illness acquired in the United States—major pathogens. 2011. Emerg Infect Dis. 17 (1): 126-8.

Gandhi M, Chikindas ML. 2007. *Listeria*: A foodborne pathogen that knows how to survive. Int J Food Microbiol. 113 (1): 1-15.

USDA-FSIS. 2011. Isolation and Identification of *Listeria monocytogenes* from red meat, poultry, egg, and environmental samples. In: Microbiology Laboratory Guidebook, Chapter 8.07. (http://www.fsis.usda.gov/PDF/MLG_8_07.pdf).

Examination Report from UK Application No. GB1305471.3 dated Jan. 10, 2014, 2 pages.

\* cited by examiner

CULTURE MEDIUM, METHOD FOR CULTURING *LISTERIA*, AND METHOD FOR DETECTING *LISTERIA*

BACKGROUND

1. Field

The subject matter disclosed generally relates to media and methods to culture microorganisms and to detecting microorganisms.

2. Related Publications

U.S. patent application Ser. No. 10/597,909, SELECTIVE GROWTH MEDIUM FOR *LISTERIA* SPP, filed on Feb. 12, 2005, discloses compositions comprising Lithium Chloride and selective agents.

Mendonca, A., F. and Knabel, S., J. 1994. A novel strictly anaerobic recovery and enrichment system incorporating lithium for detection of heat-injured *Listeria monocytogenes* in pasteurized milk containing background microflora. Appl. Environ. Microbiol. 60: 4001-4008.

Beumer R. R., te Giffel M. C, Anthonie S. V. R., Cox L. J. 1996. The effect of acriflavine and nalidixic acid on the growth of *Listeria* spp. in enrichment media. F. Microbiol. 13 (2): 137-148.

Teo, A., Y-L., Knabel, S., J. 2000. Development of a Simple Recovery-Enrichment System for Enhanced Detection of Heat-Injured *Listeria monocytogenes* in Pasteurized Milk. J. Food Prot. 63 (4): 462-472.

Busch S V, Donnelly C W. Development of a repair-enrichment broth for resuscitation of heat-injured *Listeria monocytogenes* and *Listeria innocua*. 1992. Appl. Environ. Microbiol. 58 (1):14-20.

Buchrieser C, Rocourt J. 2007. The genus *Listeria* and *Listeria monocytogenes*: phylogenetic position, taxonomy, and identification. In: *Listeria*, listeriosis, and food safety, $3^{rd}$ edition./Ed. by Ryser E T, Marth E H. CRC Press. 896 p.

Lang Halter E, Neuhaus K, Scherer S. 2012. *Listeria weihenstephanensis* sp. nov., isolated from the water plant *Lemna trisulca* of a German fresh water pond. Int J Syst Evol Microbiol. April 27. [Epub ahead of print].

Bertsch D, Rau J, Eugter M R, Haug M C, Lawson P A, Lacroix C, Meile L 2012. *Listeria fleischmannii* sp. nov., isolated from cheese. Int J Syst Evol Microbiol. April 20. [Epub ahead of print].

Painter J, Slutsker L. Listeriosis in humans. 2007. The genus *Listeria* and *Listeria monocytogenes*: phylogenetic position, taxonomy, and identification. In: *Listeria*, listeriosis, and food safety, 3rd edition./Ed. by Ryser E T, Marth E H. CRC Press. 896 p.

Wesley I V. Listeriosis in animals. 2007. The genus *Listeria* and *Listeria monocytogenes*: phylogenetic position, taxonomy, and identification. In: *Listeria*, listeriosis, and food safety, 3rd edition./Ed. by Ryser E T, Marth E H. CRC Press. 896 p.

Ramaswamy V, Cresence V M, Rejitha J S, Lekshmi M U, Dharsana K S, Prasad S P, Vijila H M. 2007. *Listeria*—review of epidemiology and pathogenesis. J Microbiol Immunol Infect. 40 (1): 4-13.

Koch J, Stark K. Significant increase of listeriosis in Germany-epidemiological patterns 2001-2005. (2006). Euro Surveill. 11 (6): 85-8.

Anonymous Incidence of Foodborne Illness, 2010. (website: cdc.gov/Features/dsFoodborneIllness.

EU summary report on trends and sources of zoonoses and zoonotic agents and food-borne outbreaks 2009. (website: efsa.europa.eu/en/efsaioumal/doc/2090.pdf.

Scallan E, Hoekstra R M, Angulo F J, Tauxe R V, Widdowson M-A, Roy S L, Jones J L, Griffin P M. Foodborne illness acquired in the United States—major pathogens. 2011. Emerg Infect Dis. 17 (1): 126-8.

Gandhi M, Chikindas M L. 2007. *Listeria*: A foodborne pathogen that knows how to survive. Int J Food Microbiol. 113 (1): 1-15.

USDA-FSIS. 2011. Isolation and Identification of *Listeria monocytogenes* from red meat, poultry, egg, and environmental samples. In: Microbiology Laboratory Guidebook, Chapter 8.07. (website: www.fsis.usda.gov/PDF/MLG 8 07.pdf.

SUMMARY

In an embodiment there is disclosed culture medium comprising biologically effective concentrations of: unchelated magnesium ions; and an oxygen scavenger.

In alternative embodiments the oxygen scavenger is selected from the group consisting of a pyruvate salt, catalase, a thioglycolate salt, cysteine, Oxyrase™, $Na_2S$, and FeS.

In alternative embodiments the medium further comprises a biologically effective concentration of: lithium salt; or an iron (III) salt; or a lithium salt and an iron (III) salt, in alternative embodiments the medium further comprises a selective agent.

In alternative embodiments the medium further comprises a substantially non magnesium chelating buffer.

In alternative embodiments the medium is for culturing *Listeria* spp.

In alternative embodiments
said iron (III) salt is present at a concentration of greater than about 0.05 g/L;
said Lithium salt is present at a concentration of greater than about 0.1 g/L;
said Magnesium salt is present at a concentration of greater than about 0.1 g/L; and
said oxygen scavenger is present at a concentration of greater than about 0.1 g/L.

In alternative embodiments the medium further comprises a selective agent.

In an embodiment there is disclosed a method for culturing a biological sample, the method comprising: culturing the sample in a medium comprising biologically effective concentrations of unchelated magnesium ions and an oxygen scavenger.

In alternative embodiments of the method the medium comprises a lithium salt; or an iron (III) salt; or a lithium salt and an iron (III) salt.

In alternative embodiments of the method the medium further comprises a selective agent.

In alternative embodiments of the method
said iron (III) salt is present at a concentration of greater than about 0.05 g/L;
said Lithium salt is present at a concentration of greater than about 0.1 g/L;
said Magnesium salt is present at a concentration of greater than about 0.1 g/L; and
said oxygen scavenger is present at a concentration of greater than about 0.1 g/L.

In alternative embodiments the method is for culturing *Listeria* spp.

In an embodiment there is disclosed a method for detecting bacteria in a sample, the method comprising the step of culturing the sample in the presence of biologically effective concentrations of: a) unchelated magnesium ions, and b) an oxygen scavenger.

In an embodiment of the method the oxygen scavenger is selected from the group consisting of a pyruvate salt, catalase, a thioglycolate salt, cysteine, Oxyrase™, $Na_2S$, and FeS.

In an embodiment of the method the culturing occurs in the presence of:
a) a lithium salt; or
b) an iron (III) salt; or
c) a lithium salt and an iron (III) salt.

In an embodiment of the method the culturing occurs in the presence of a selective agent.

In an embodiment of the method the bacteria are *Listeria* spp.

In an embodiment there is disclosed a composition for supplementing a culture medium, the composition comprising a non-magnesium chelating buffer and an oxygen scavenger.

In alternative embodiments the composition further comprises a biologically effective concentration of:
a) a lithium salt; or
b) an iron (III) salt; or
c) a lithium salt and an iron (III) salt.

In alternative embodiments there is disclosed the use of the composition to culture *Listeria* spp.

In an embodiment there is disclosed a powdered culture medium suitable for dilution to yield a liquid culture medium comprising biologically effective amounts of unchelated magnesium ions and an oxygen scavenger.

In alternative embodiments of the powdered culture medium, the diluted medium further comprises biologically effective amounts of:
a) a lithium salt; or
b) an iron (III) salt; or
c) a lithium salt and an iron (III) salt.

In an embodiment there is disclosed a kit for culturing *Listeria* spp., the kit comprising an oxygen scavenger and a non-magnesium chelating buffer.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF SELECTED EMBODIMENTS

Terms

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.).

In this disclosure the singular forms an "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

In this disclosure, unless otherwise indicated, all numbers expressing quantities or ingredients, measurement of properties and so forth used in the specification and claims are to be understood as being modified in all instances by the term "about". Accordingly, unless indicated to the contrary or necessary in light of the context, the numerical parameters set forth in the disclosure are approximations that can vary depending upon the desired properties sought to be obtained by those skilled in the art utilizing the teachings of the present disclosure and in light of the inaccuracies of measurement and quantification. Without limiting the application of the doctrine of equivalents to the scope of the claims, each numerical parameter should at least be construed in light of the number of reported significant digits and by applying ordinary rounding techniques. Not withstanding that the numerical ranges and parameters setting forth the broad scope of the disclosure are approximations, their numerical values set forth in the specific examples are understood broadly only to the extent that this is consistent with the validity of the disclosure and the distinction of the subject matter disclosed and claimed from the prior art.

In this disclosure the term "POD" means probability of difference and the term "dPOD" means difference in probability of difference.

In this disclosure the term "Sensitivity" or "Rate of sensitivity" is defined as: Rate of sensitivity=(number of Actero *Listeria* method positive environmental samples/Number of positive environmental samples confirmed by second enrichment)×100%.

In this disclosure the term "Specificity" or "Rate of specificity" is defined as: Rate of specificity=(Number of Actero *Listeria* method negative environmental samples/Number of negative environmental samples confirmed by second enrichment)×100%.

In this disclosure the term "Method Agreement" is defined as: method agreement=[1−|(Number of Actero *Listeria* method true positive and true negative test samples−Number of reference method true positive and true negative test samples)/Total no. of method samples|]×100%.

In this disclosure the term "Accuracy" is defined as: Accuracy=[Number of confirmed Actero *Listeria* method positive test samples/Number of reference method positive test samples]×100%.

In this disclosure the term "media", "medium", "broth", "culture broth" and the like all refer to a nutrient mixture suitable to culture a desired microorganism which may be a bacteria or microbe strain or species. In particular embodiments media may comprise one or more of water, agar, proteins, amino acids, caesein hydrolysate, salts, lipids, carbohydrates, salts, minerals, and pH buffers and may contain extracts such as meat extract, yeast extract, tryptone, phytone, peptone, and malt extract, and may comprise luria bertani (LB) medium. In embodiments media may be simple, complex or defined media and may be enriched media and may be supplemented in a wide variety of ways, ail of which will be readily understood by those skilled in the art. In embodiments the media may comprise MOPS buffer, an Iron (III) salt such as ferric citrate, a magnesium salt such as Magnesium sulphate, a lithium salt such as lithium chloride, and may contain pyruvate. In embodiments media may comprise or consist of any core media as defined herein. In embodiments media may be simple, complex or defined media and may be enriched media and may be supplemented in a wide variety of ways, all of which will be readily understood by those skilled in the art. The terms "Actero/*Listeria*" and "ALEM" broth, medium, enrichment medium and the like are used as general descriptors for media according to embodiments hereof.

In embodiments media contain a pH buffer which may be a non-Magnesium chelating buffer. In one series of embodiments the pH buffer is a mixture of MOPS sodium salt and MOPS free acid, but a range of other buffers such as Carbonate and Phosphate buffers may be useable in alternative embodiments and will be readily selected amongst and implemented by those skilled in the art, to achieve a desired pH for the medium.

In embodiments media may be provided in the form of a powder or concentrate, also generally referred to as "powdered medium", "medium powder", "medium concentrate", "concentrated medium" or the like, comprising a plurality of components and suitable to be combined with a predetermined volume of water to provide a liquid medium with desired concentrations of the particular components. Such a powdered medium or concentrated medium may be complete, meaning that it need only be dissolved in suitable water, normally sterile water, before use. Alternatively in embodiments a powdered or concentrated medium may be partial, meaning that additional components need to be added to provide a complete medium suitable for use. In embodiments a powdered or concentrated medium also includes medium that is at least partly hydrated in concentrated form suitable for dilution to produce the medium for actual use in culturing bacteria. It will be understood that term "medium" or "media" as used herein, unless otherwise required by the context, includes both the final media having components at concentrations suitable for culturing bacteria and microorganisms, and powdered or concentrated media suitable for dilution.

In this disclosure the term "oxygen scavenger" means a chemical that will remove or inactivate free oxygen or oxygen radicals. In particular embodiments an oxygen scavenger is selected from the group consisting of a pyruvate salt, catalase, a thioglycolate salt or compound, cysteine, L-(+)-cysteine hydrochloride, L-cysteine, Oxyrase™ (Patel, 1995) $Na_2S$ and FeS. In embodiments particular oxygen scavengers are laevorotatory or dextrotatory (L or D) forms and may be racemic forms or mixtures. Those skilled in the art will readily select from such alternatives and will recognise that such oxygen scavengers will be selected amongst based on their biological compatibility for the embodiment in question. In embodiments where an oxygen scavenger or any other reagent referred to in this disclosure is a salt then any biologically effective and compatible salt is useable and unsuitable salts will be readily, identified and avoided by those skilled in the art. In embodiments salts are sodium or potassium salts.

In this disclosure the term "pyruvate salt" means and includes ail salts of pyruvic acid (also known as 2-oxo-propanoic acid) and any compounds comprising a pyruvate anion, and any biologically effective isomers or substituted forms thereof. In embodiments the pyruvate salt is sodium or potassium pyruvate. Those skilled in the art will readily identify and avoid salts which are not biologically effective or desirable, for example due to toxicity.

Those skilled in the art will readily appreciate that salts and other compounds that are lethal or deleterious to the bacteria of interest will be avoided and such salts and compounds will be readily identified by those skilled in the art.

In this disclosure an alkali metal means any one of Lithium, Sodium, Potassium, Rubidium, Caesium, and Francium and an alkali metal salt means any biologically acceptable salt of any of the foregoing. In embodiments a salt is soluble and may be organic or inorganic, and by way of example may be chloride, phosphate, nitrate, hydrogen carbonate, pyruvate, ethanoate.

In this disclosure the verb "buffer" means stabilizing the pH of a solution, which may be a culture medium, in a predetermined range, in ways that will be readily apparent those skilled in the art. The noun "buffer" means a chemical suitable to stabilize the pH of a solution.

In this disclosure the term "salt" refers to salts that are soluble or are substantially or partially soluble under the relevant conditions.

In this disclosure reference to "growing" or "culturing" a sample or microorganism means a process whereby the sample or microorganism is held under conditions suitable or substantially suitable for supporting or promoting growth or division of one or more microorganisms of interest. It will be understood that these terms include a situation wherein a sample is exposed to the relevant conditions whether or not a microorganism of interest is actually present, or is present in detectable amounts.

In this disclosure the term "salt" refers to any biologically compatible salt that is soluble or substantially soluble or is soluble to the degree necessary to have the desired biological effectiveness under applicable culture conditions.

In this disclosure a "non-magnesium chelating buffer" or "substantially non-magnesium chelating buffer" means a buffer which does not substantially chelate or sequester dissolved Magnesium ions from solution or does not do so to a biologically significant extent. In particular embodiments a non-magnesium chelating buffer is or comprises 3-(n-Morpholino)Propanesulfonic Acid, also referred to as 3-morpholinopropane-1-sulfonic acid; 3-(N-morpholino)propanesulfonic acid; 3-N-morpholino propansulfonic acid; 4-Morpholinepropanesulfonic acid and "MOPS" or is or comprises a mixture of MOPS Sodium salt and MOPS free acid. In alternative embodiments a range of biologically acceptable non-magnesium chelating buffers may be used and will be readily identified and selected amongst by those skilled in the art. In some embodiments such buffers are substituted or otherwise chemically modified forms of MOPS. Similarly "unchelated" or "non-chelated" refers to an ion or chemical that is substantially free in solution.

In this disclosure the term "base" or "core" medium or broth refers to a partial broth comprising certain basic required components readily recognised by those skilled in the art and whose detailed composition may be varied substantially while remaining suitable to support the growth of any microorganism of interest. Thus in embodiments, core medium comprises salts, buffer, and protein extract, and in embodiments comprises carbonate or phosphate or MOPS buffers or may comprise, sodium salts, magnesium salts and calcium salts. In embodiments a liter of core medium has the recipe shown in Table 1. However in alternative embodiments core media comprise one or more of water, agar, proteins, amino acids, casein hydrolysate, salts, lipids, carbohydrates, salts, minerals, and pH buffers and in embodiments contains extracts such as meat extract, yeast extract, tryptone, phytone, peptone, and malt extract, and in embodiments medium isbe or comprises luria bertani (LB) medium; low salt LB medium (1% peptone, 0.5% yeast extract, and id 0.5% NaCl), SOB medium (2% peptone, 0.5% Yeast extract, 10 mM NaCl, 2.5 mM KCl 10 mM $MgCl_2$, 10 mM $MgSO_4$), SOC medium (2% peptone, 0.5% Yeast extract, 10 mM NaCl, 2.5 mM KCl, 10 mM MgCl$_2$, 10 mM MgSO$_4$, 20 mM Glucose), Superbroth (3.2% peptone, 2% yeast extract, and 0.5% NaCl), 2×TY medium (1.6% peptone, 1% yeast extract and 0.5% NaCl), TerrificBroth (TB) (1.2% peptone, 2.4% yeast extract, 72 mM K2HPO4, 17 mM KH2PO4, and 0.4% glycerol), LB Miller broth or LB Lennox broth (1% peptone, 0.5% yeast extract, and 1% NaCl).

TABLE 1

Generic content of base media

| Ingredients | Manufacturers | Quantity (g/L) |
|---|---|---|
| Phytone | BD BBL (211906) | X to Y |
| Tryptone | Oxoid (LP0042) | X to Y |
| Beef extract | BD BBL (212303) | X to Y |
| Yeast extract | BD Bacto (212750) | X to Y |

In Table 1, X and Y are numerical values expressed in grams. Each of X and Y may independently be 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20 or more grams and in particular embodiments the range X to Y may be delimited by any values of X and Y. It will be understood that in particular embodiments modified forms of phytone, tryptone, beef extract and yeast extract will be readily selected from by those skilled in the art, as will suitable substitutes for the foregoing. In some embodiments alternative salts of magnesium, calcium and sodium may be used and in particular embodiments alternatives to magnesium, calcium and sodium may be selected. In some embodiments buffers will be included the core medium and in embodiments the buffer is a MOPS buffer. Those skilled in the art will readily make suitable adjustments to the recipe for base medium to suit particular purposes. It will be understood that any and all variants on the base medium that are compatible with the effectiveness of the enrichment disclosed herein, are intended to be included within the scope of the subject matter claimed.

TABLE 2

Shows the recipe for base media according to a particular embodiment.

| Ingredients | Quantity (g/L) |
|---|---|
| Phytone | 5 |
| Tryptone | 5 |
| Beef extract | 5 |
| Yeast extract | 5 |

Those skilled in the art will readily understand that the growth of a desired microorganism will be best promoted at selected temperatures suited to the microorganism in question. In particular embodiments the desired microorganism is *Listeria*, spp and the culturing may be carried out at about 29° C., 30° C., 31° C., 32° C., 33° C., 34° C., 35° C., 36° C., 37° C., 38° C., 39° C., 40° C., 41° C., 42° C., 43° C. or more and the broth to be used is or may be pre-warmed to this temperature preparatory to inoculation with a sample for testing. In particular embodiments culturing may be carried out at about 35° C. and the broth to be used may be pre-warmed to this temperature preparatory to inoculation with a sample for testing. In embodiments disclosed herein, culturing may be carried out at any temperature between 29° C. and 43° C. and may be carried out at about 29° C., 30° C., 31° C., 32° C., 33° C., 34° C., 35° C., 36° C., 37° C., 38° C., or 39° C., or 40° C., or 41° C. or 42° C. or 43° C. or between 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., 40° C. and 41° C., 41° C. and 42° C., or 42° C. and 43° C. or at a temperature of between 34° C. and 43° C., or between 35° C. and 42° C., or between 36° C. and 42° C., 38° C. and 42° C. or between 39° C. and 41° C. or between 39° C. and 40° C. or between 38° C. and 39° C., or between 39° C. and 40° C., or between 40° C. and 41° C., or between 41° C. and 42° C. or between 42° C. and 43° C. In embodiments the temperature is between 32° C. and 38° C., or between 33° C. and 37° C. In this disclosure "enrichment" of a media refers to the addition of selected components to promote the growth or other characteristics of one or more desired microorganisms. An "enrichment solution" refers to a solution comprising these additional components. In embodiments the components included in an enrichment solution include one or more of MOPS, Fe(III) salt, Lithium salt, pyruvate, and in embodiments a selective enrichment supplement comprises one or more selective agents such as nalidixic acid, cycloheximide, and acriflavine hydrochloride. In particular embodiments the enriched broth contains one or more of Magnesium sulphate, Lithium Chloride, Ferric Citrate, Sodium pyruvate and enrichment supplement.

TABLE 3

Shows the general composition of one embodiment of enriched medium.

| Ingredients | Manufacturers | Quantity (g/L) |
|---|---|---|
| Mops-sodium salt | Sigma (M9381) | X-Y |
| Mops-free acid | Sigma (M1254) | X-Y |
| Ferric citrate III | Sigma (F6129) | X-Y |
| Lithium chloride | Sigma (L4408) | X-Y |
| M$_g$SO$_4$ | BDH (BDH0246) | X-Y |
| Sodium pyruvate | Sigma (15990) | X-Y |
| Selective enrichment Supplement | Oxoid (SR0141E) | 2.7 mL |
| Composition of selective enrichment supplement (components of which are also referred to herein collectively or individually as a "selective agent" or a "selection agent" or a "selecting agent") Cycloheximide Nalidixic acid Acriflavine hydrochloride | CAS number 66-81-9 3374-05-8 8048-52-0 | quantity g/L in final enriched broth A-B A-B A-B |

Each of X and Y may independently be 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29 or 30 grams or any value therebetween and in particular variant embodiments the range X to Y may be delimited by any values of X and Y. It will be understood that the relative quantities of MOPS salt and MOPS free acid will be adjusted as necessary to achieve the desired pH.

Each of A and B may independently be 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000; 90,000 or 100,000 mg/liter.

TABLE 4

Shows the composition of a particular embodiment of enrichment medium.

| Ingredients | Manufacturers | Quantity (g/L) |
|---|---|---|
| Mops-sodium salt | Sigma (M9381) | 13.7 |
| Mops-free acid | Sigma (M1254) | 8.5 |
| Ferric citrate III | Sigma (F6129) | 0.50 |
| Lithium chloride | Sigma (L4408) | 8 |
| $M_gSO_4$ | BDH (BDH0246) | 2 |
| Sodium pyruvate | Sigma (15990) | 1 |
| Selective enrichment Supplement (also referred to herein as a "selective agent") comprising the following components: | Oxoid (SR0141E) | 2.7 mL |
| Cycloheximide | 66-81-9 | 33.75 mg |
| Nalidixic acid | 3374-05-8 | 27 mg |
| Acriflavine hydrochloride | 8048-52-0 | 10.125 mg |

*Reconstitute one vial as directed, and add 2.7 mL of the contents to 1 L of media.

However, it will be readily understood by those skilled in the art that these quantities may be varied to suit particular requirements, and in alternative embodiments the final enriched media contains about $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, $9\times10^{-6}$, $1\times10^{-5}$, $2\times10^{-5}$, $3\times10^{-5}$, $4\times10^{-5}$, $5\times10^{-5}$, $6\times10^{-5}$, $7\times10^{-5}$, $8\times10^{-5}$, $9\times10^{-5}$, $1\times10^{-4}$, $2\times10^{-4}$, $3\times10^{-4}$, $4\times10^{-4}$, $5\times10^{-4}$, $6\times10^{-4}$, $7\times10^{-4}$, $8\times10^{-4}$, $9\times10^{-4}$, $1\times10^{-3}$, $2\times10^{-3}$, $3\times10^{-3}$, $4\times10^{-3}$, $5\times10^{-3}$, $6\times10^{-3}$, $7\times10^{-3}$, $8\times10^{-3}$, $9\times10^{-3}$, $1\times10^{-2}$, $2\times10^{-2}$, $3\times10^{-2}$, $4\times10^{-2}$, $5\times10^{-2}$, $6\times10^{-2}$, $7\times10^{-2}$, $8\times10^{-2}$, $9\times10^{-2}$, $1\times10^{-1}$, $2\times10^{-1}$, $3\times10^{-1}$, $4\times10^{-1}$, $5\times10^{-1}$, $6\times10^{-1}$, $7\times10^{-1}$, $8\times10^{-1}$, $9\times10^{-1}$, 10, 20, 30, 40, 50, 60, 70, 80, 90, $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, or more or less g/liter or mg/liter of individual components in the broths.

In this disclosure a "supplement" for a culture media means a solution, liquid, solid or other material for addition to a culture medium. A supplement has the effect or purpose of promoting the growth of one or more microorganisms and in specific embodiments selectively promotes the growth of one or more microorganisms relative to other, non-desired microorganisms. In particular embodiments a supplement comprises one or more of a magnesium salt, a lithium salt, an iron(III) salt, a pyruvate and a selective agent, or comprises precursors or modified forms that may be readily converted or metabolised to form any of the foregoing. In embodiments a supplement is a supplement for promoting the growth of *Listeria* spp. In this disclosure the term "selective agent" means a chemical or culture condition which serves to favour the growth of a desired microorganism or to inhibit the growth of an undesired microorganism. In particular embodiments selective agents include antibiotics, sulphanamides or antiseptics. In particular embodiments a selective agent is or comprises one, two or all three of nalidixic acid, cycloheximide and acriflavine hydrochloride or includes suitable equivalents or alternatives thereto. The term "selective enrichment supplement" is equivalent to the term "selective agent". In particular embodiments the working concentration of cycloheximide is about 33.75 mg per liter of culture medium, and in alternative embodiments is between 15 and 50 mg/liter of culture medium, or may be greater than 5, 10, 15, 20, 25, 30, 35, 40, 45, 50, 55, 60, 65, 70, 75, 80, 85, 90, 95, 100 or more mg/liter of culture medium. In particular embodiments the working concentration of nalidixic acid is about 27 mg per liter of culture medium, or is between 10 and 50 mg/liter of culture medium or is greater than 5, 10, 15, 20, 25, 30, 35, 40, 45, 50, 55, 60, 65, 70, 75, 80, 85, 90, 95, 100 or more mg/liter of culture medium. In embodiments the working concentration of acriflavine hydrochloride is about 10,125 mg/liter, or is between 6000 and 15,000 mg/liter, or is greater than 1000, 2000, 3000, 4000, 5000, 6000, 7000, 8000, 9000, 10000, 11000, 12000, 13000, 14000, 15000, 16000, 17000, 18000, 19000, 20000 or more mg/liter of culture medium. Those skilled in the art will, however, recognise that a wide variety of concentrations of selective agents may be employed and will make suitable adjustments for particular purposes.

In this disclosure the terms "Actero/*Listeria*" "Actero *Listeria*", and "ALEM", broth, medium, enrichment broth and the like, all refer to the broth or media according to embodiments hereof.

In this disclosure "culture conditions" means the parameters for the culturing of a microorganism, and includes the chemical composition and physical properties of the culture medium as well as the temperature, agitation, containment, and duration of the culture. Thus in particular alternative embodiments, a culture is maintained at any temperature between 29° C. and 43° C. and in particular embodiments is maintained at a temperature of about 39° C. It will be understood that in certain embodiments temperatures above 30° C. and below 25° C. and in embodiments is maintained at temperatures between 29° C. and 43° C. and may be carried out at about 29° C., 30° C., 31° C., 32° C., 33° C., 34° C., 35° C., 36° C., 37° C., 38° C., or 39° C., or 40° C., or 41° C. or 42° C. or 43° C. or between 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., 40° C. and 41° C., 41° C. and 42° C., or 42° C. and 43° C. or at a temperature of between 34° C. and 43° C., or between 35° C. and 42° C., or between 36° C. and 42° C., 38° C. and 42° C. or between 39° C. and 41° C. or between 39° C. and 40° C. or between 38° C. and 39° C., or between 39° C. and 40° C., or between 40° C. and 41° C., or between 41° C. and 42° C. or between 42° C. and 43° C. In embodiments the temperature is between 32° C. and 38° C., or between 33° C. and 36° C. may also be used to culture microorganisms using the media disclosed herein, however it has been found that temperatures outside the range between about 25° C. and about 30° C. may allow faster growth of other non-desired microorganisms and may inhibit the growth of *Listeria*. The pH of culture medium is generally set at between 7 and 8 and for example in particular embodiments may be about 7.0, 7.1, 7.2, 7.3, 7.4, 7.5, 7.6, 7.7, 7.8, 7.9 or 8.0 or is in a range delimited by any two of the foregoing values. It will be understood that a pH outside of the range pH7-8 may still be useable in embodiments, but that the efficiency and selectivity of the culture may be adversely affected. A culture may be grown for any desired period following inoculation with a sample but it has been found that in non-limiting embodiments a 24 hour culture period is sufficient to enrich the content of *Listeria* spp sufficiently to permit testing by normal methods. However, in alternative embodiments for particular purposes the culture period may be longer or shorter and may be up to or less than 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more hours. Those skilled in the art will readily select a suitable culture period to satisfy particular requirements.

In this disclosure a "microorganism" means a bacterium, which may be a pathogenic bacterium and in embodiments may be *Listeria* spp.

In this disclosure "detecting" a microorganism, means any process of observing the presence of a microorganism, or a change in the presence of a microorganism, in a biological sample, whether or not the microorganism or the change in the microorganism is actually detected. In other words, the act of testing a sample for a microorganism or a change in the level of a microorganism, is a "detection" even if the microorganism is determined to be not present or below the level of sensitivity. Detection may be a quantitative, semi-quantitative or non-quantitative observation and may be based on a comparison with one or more control samples. Detection may be applied to any sample wherein the presence or absence of the microorganism is to be assessed, and in particular embodiments but without limiting the generality of the foregoing, a sample may be or may comprise any form of biological material and may comprise ground, or unground, meat, poultry, fish, seafood, vegetables, fruit, dairy produce, milk, eggs, packaged food, canned food, bottled food, or wrapped food.

In embodiments and without limitation, the step of detecting a microorganism comprises: using PCR, real-time PCR, lectins, simple diffusion, lateral diffusion, immunological detection, lateral flow, or flow through methods to detect the presence of the microorganism in a culture. By way of illustration and not limitation, in particular embodiments possible detecting methods include or use the subject matter disclosed in any of U.S. Pat. No. 6,483,303; U.S. Pat. No. 6,597,176; U.S. Pat. No. 6,607,922; U.S. Pat. No. 6,927,570; and U.S. Pat. No. 7,323,139.

In this disclosure the terms "sample" and "biological sample" have the same and broadest possible meaning consistent with their context and refer generally and without limitation to anything desired to be tested for the presence of one or more microorganisms of interest, and include all such subject matter whether or not it actually contains any microorganisms, or any microorganisms of interest and whether or hot it contains *salmonella* spp. or *E. coli* spp. In embodiments sample may be obtained by taking a piece or portion, or by use of a swab, wipe, filter, smear, or any other suitable method, all of which will be readily understood and implemented and selected among by those skilled in the art. In particular embodiments a sample is or comprises food material or is or comprises plant or animal material or is or comprises meat, seafood, fish, vegetables, fruit, salads, premade meals, eggs, dairy produce, combined and uncombined food materials, canned goods, or any other form of fresh, raw, cooked, uncooked, frozen, refrigerated, ground, chopped, canned, heat treated, dried, preserved, refined, or preserved foodstuffs whatsoever. In further embodiments a sample may be taken from an environment, surface, container or location wherein it is desired to determine whether a microorganism of interest is present/for example and without limitation kitchen surfaces, cooking surfaces, food storage containers, eating utensils, refrigerators, freezers, display containers, wrapping materials, live plants and animals and any other environment, location, surface, or material whatsoever that may be of interest to a user. Those skilled in the art will understand and implement suitable methods for selecting, obtaining and handling any sample for use in embodiments. In selected embodiments samples are samples of meat, fish, seafood, vegetables, eggs or dairy produce.

Culture Medium According to an Embodiment

In the embodiment there is disclosed a culture medium comprising biologically effective concentrations of unchelated magnesium ions; and of an oxygen scavenger. It will be understood that the term "biologically effective concentration" describes the concentrations of both the unchelated magnesium ions and of the oxygen scavenger, and that both such concentrations may optionally be adjusted in ways readily recognized by those skilled in the art, but that such adjustments will be made in ways which preserve the effectiveness of the combination for the purposes of particular embodiments. In embodiments the oxygen scavenger is selected from the group consisting of a pyruvate salt, catalase, a thioglycolate salt, cysteine, Oxyrase™, Na2S, and FeS.

In an embodiments the culture medium comprises a biologically effective concentration of unchelated magnesium ions and a biologically effective concentration of at least one component selected from the group consisting of: a lithium salt, an iron(III) salt, and a pyruvate salt. In variant embodiments the medium comprises a biologically effective combination of at least two, three or four components selected from the group consisting of a lithium salt, a magnesium salt, an iron(III) salt, and a pyruvate salt. In variant embodiments the medium further comprises one or more selective agents. In variant embodiments the medium is a buffered/medium and in variant embodiments the buffer substantially non-magnesium chelating. In embodiments the iron (III) salt is present at a concentration of greater than about 0.05 g/L; the Lithium salt is present at a concentration of greater than about 0.1 g/L; the Magnesium salt is present at a concentration of greater than about 0.1 g/L; and the pyruvate salt is present at a concentration of greater than about 0.1 g/L. In embodiments the medium is for culturing *Listeria* spp.

In further alternative embodiments the medium comprises at least three, four, five or all six components selected from the group consisting of a non-magnesium chelating buffer, a lithium salt, a magnesium salt, an iron(III) salt, and a pyruvate salt. In alternative embodiments one of the selected components is a lithium salt. In a further alternative embodiment one of the selected components is a non-magnesium chelating buffer. In a further alternative embodiment one of the selected components is a magnesium salt. In a further alternative embodiment one of the selected components is an iron (III) salt. In a further alternative embodiment one of the selected components is a pyruvate salt.

In a further series of alternative embodiments the selected components comprise a non-magnesium chelating buffer, a lithium salt and at least one component selected from the group consisting of a magnesium salt, an iron(III) salt, and a pyruvate salt.

In a further series of alternative embodiments the selected components comprise a non-magnesium chelating buffer, a magnesium salt and at least one component selected from the group consisting of a lithium salt, an iron(III) salt, and a pyruvate salt.

In a further series of alternative embodiments the selected components comprise a non-magnesium chelating buffer, a iron (III) oxide salt and at least one component selected from the group consisting of a magnesium salt, a lithium salt, and a pyruvate salt.

In a further series of alternative embodiments the selected components comprise a non-magnesium chelating buffer, a pyruvate salt and at least one component selected from the group consisting of a magnesium salt, a lithium salt, and an iron (III) oxide salt.

In a further series, of alternative embodiments the selected components comprise a lithium salt and a non-magnesium chelating buffer, or a lithium salt and a magnesium salt or a lithium salt and an iron (III) salt, or a lithium salt and a pyruvate salt. In a further series of selected embodiments the selected components comprise a pyruvate salt and non-magnesium chelating buffer, or pyruvate salt and magnesium salt, or a pyruvate salt and a lithium salt or a pyruvate salt and an iron (III) oxide salt. In a further series of selected embodiments the selected components comprise an iron (III) oxide salt and lithium salt, or an iron (III) oxide salt and pyruvate salt, or an iron (III) oxide salt and non-magnesium chelating buffer, or an iron (III) oxide salt and magnesium salt.

In further series of embodiments the medium further comprises a selective agent. In embodiments the selective agent comprises at least one of nalidixic acid, acriflavine hydrochloride and cycloheximide. In embodiments the iron (III) salt is present at a concentration of greater than about 0.05 g/L; Lithium salt is present at a concentration of greater than about 0.1 g/L; the Magnesium salt is present at a concentration of greater than about 0.1 g/L; and the pyruvate salt is present at a concentration of greater than about 0.1 g/L. In embodiments the iron (III) salt is present at a concentration of between 0.05 g/L and 50 g/L; said Lithium salt is present at a concentration of between 0.1 g/L and 100 g/L; said Magnesium salt is present at a concentration of between 0.1 g/L and 100 g/L; said pyruvate salt is present at a concentration of between 0.1 g/L and 100 g/L.

The composition of a medium according to one example of the culture medium according to embodiments is shown in Table 5.

TABLE 5

The composition of culture medium according to an example of an embodiment.

| Ingredients | Manufacturers | Quantity (g/L) |
| --- | --- | --- |
| Phytone | BD BBL (211906) | 5 |
| Tryptone | Oxoid (LP0042) | 5 |
| Beef extract | BD BBL (212303) | 5 |
| Yeast extract | BD Bacto (212750) | 5 |
| Mops-sodium salt | Sigma (M9381) | 13.7 |
| Mops-free acid | Sigma (M1254) | 8.5 |
| Ferric citrate III | Sigma (F6129) | 0.5 |
| Lithium chloride | Sigma (L4408) | 8 |
| MgSO$_4$ | BDH (BDH0246) | 2 |
| Sodium pyruvate | Sigma (15990) | 1 |
| Selective supplement (one or more components of which are also referred to herein as a "selective agent"). The selective supplement comprises each of cycloheximide, nalidixic acid and acriflavine hydrochloride | Oxoid (SR0141E) | 2.7 mL |

*Reconstitute one vial as directed, and add 2.7 mL of the contents to 1 L of media.

The 2.7 ml of selective supplement comprises 33.75 mg of cycloheximide, 27 mg of nalidixic acid and 10.125 mg of acriflavine hydrochloride.

Sterilize the media with the supplement added by autoclaving at 110° C. for 15 minutes.

Methods of Culturing According to an Embodiment

In the embodiment there is disclosed a method for culturing a biological sample, the method comprising culturing the sample in the presence of biologically effective concentrations of: unchelated magnesium ions; and an oxygen scavenger. In embodiments the oxygen scavenger is selected from the group consisting of a pyruvate salt, catalase, a thioglycolate salt, cysteine, Oxyrase™, Na2S, and FeS.

In variants of the embodiment there is disclosed a method for culturing a biological sample the method comprising: culturing the sample in a medium comprising a biologically effective concentration of unchelated magnesium ions and a biologically effective concentration of at least one component selected from the group consisting of: a lithium salt, an iron (III) salt, and a pyruvate salt. In alternative embodiments the culturing occurs in the presence of at least two, three, four, five, or six components selected from the group consisting of a substantially non-magnesium chelating buffer, a magnesium salt, a lithium salt, an iron(III) salt, a pyruvate salt, and a selective agent. In embodiments the method comprises culturing the bacteria in a medium according to the first embodiment. In embodiments the detecting further comprises a PCR, lectin binding, simple diffusion, lateral diffusion, immunological detection, lateral flow, or flow through step. In embodiments the culturing occurs in the presence of a selective agent. In embodiments the bacteria are or include *Listeria* spp and in embodiments the detecting comprises preferentially culturing a bacterial species which in embodiments is or includes a *Listeria* spp. In variants of the embodiment the method comprises culturing the biological sample using media according to the embodiment. In alternative embodiments the biological sample comprises bacteria, in embodiments the bacteria are *Listeria* spp and in embodiments the method comprises preferentially culturing *Listeria* spp or other strains of bacteria.

Methods for Detecting Bacteria According to Embodiments

In the embodiment there is disclosed a method for detecting bacteria in a sample, the method comprising culturing the sample in the presence of biologically effective concentrations of: unchelated magnesium ions; and an oxygen scavenger. In embodiments the oxygen scavenger is selected from the group consisting of a pyruvate salt, catalase, a thioglycolate salt, cysteine, Oxyrase™, Na2S, and FeS.

In a further series of embodiments there are is disclosed a method for detecting bacteria in a sample, the method comprising the step of culturing the sample in the presence of a biologically effective combination of: unchelated magnesium ions, and at least one component selected from the group consisting of a lithium salt, an iron(III) salt, a pyruvate salt, and a selective agent. In alternative embodiments the culturing occurs in the presence of at least two, three, four, five, or six components selected from the group consisting of a substantially non-magnesium chelating buffer, a magnesium salt, a lithium salt, an iron(III) salt, a pyruvate salt, and a selective agent. In embodiments the method comprises culturing the bacteria in a medium according to the embodiment. In alternative embodiments the detecting further comprises a PCR, lectin binding, simple diffusion, lateral diffusion, immunological detection, lateral flow, or flow through step. In alternative embodiments the culturing occurs in the presence of a selective agent. In alternative embodiments the bacteria are Listeria spp and in embodiments the detecting comprises preferentially culturing a bacterial species which may be a Listeria spp.

In embodiments, after culturing the microorganisms in the media according to an embodiment for a suitable time period under suitable culture conditions, the presence of the microorganism of interest is detected by any one of a range of methods readily apparent to those skilled in the art. Such methods include but are not limited to PCR detection, real time PCR detection, lectin binding, simple diffusion, lateral diffusion, immunological detection, lateral flow, or flow through methods. Immunological methods may include immunoprecipitation, blotting, immunoradioassay or immuno precipitation associated with magnetic ligands, or may use any other suitable methods.

In particular embodiments an aliquot of the culture is heated or otherwise treated to kill microorganisms before testing. The heated sample may then be processed through, the desired methodology to identify the presence of antigens or nucleic acid sequences diagnostic of the microorganism of interest.

In embodiments the medium may be used in combination with existing proprietary FoodChek™ technology hereafter referred to as MICT. Broadly in one example of the use of the MICT methodology, an aliquot of the enriched culture is heated to kill the target analyte. The heated sample is loaded in a lateral flow cassette, which is composed of a sample/conjugate pad containing nano-sized magnetic particles conjugated to an antibody that will bind the pathogen's antigen. The tests also contain a second antibody in a narrow strip called the capture zone. Capillary flow takes the loaded liquid through the sample pad to the conjugate pad, where the target bacteria bind to the antibody-coated particles. This immune complex flows into the test strip to the capture zone. The result is an accumulation of magnetic particles in the capture zone. If the target pathogen is absent, immune complexes do not form, particles do not accumulate at the capture line, and the test result is negative. Further downstream, a control line that has been stripped in similar fashion but with a different reagent verifies that the test was performed correctly and that the reagents are still active. The cassette is read in an instrument capable of detecting low concentrations of magnetic particles. The detector senses small changes in a magnetic field along the test strip as it passes under a group of sensing coils. The coils are wound in alternating directions so that a characteristic signal profile is generated by the presence of magnetic particles bound to test or control lines. The instrument compares the detection signal with a positive threshold value encoded in the bar code stuck on each individual cassette, and then reports a positive or negative result, the results are displayed on the instrument's liquid crystal display screen and printed, or transferred to a related computer. In addition to all analysis parameters, the bar code also encodes the test name, lot number, and expiration date which are printed along with the test result. The detailed application and use of such detection methodology will be readily understood by those skilled in the art. Embodiments of the MICT technology for testing or determining of the presence or absence of a microorganism are set forth in one or more of U.S. Pat. No. 7,323,139, U.S. Pat. No. 6,927,570, U.S. Pat. No. 6,607,922, U.S. Pat. No. 6,597,176, U.S. Pat. No. 6,518,747, U.S. Pat. No. 6,483,303, U.S. Pat. No. 6,046,585, U.S. Pat. No. 6,275,031, U.S. Pat. No. 6,437,563, the entire disclosures of which are hereby incorporated herein by reference where permissible by law.

In embodiments, the medium can replace at least the first enrichment step in standard protocols for the isolation and identification of microorganisms and in embodiments these are Listeria spp.

Supplements According to an Embodiment

In a further series of embodiments there is disclosed a composition for supplementing a culture medium, the supplement comprising a biologically effective concentrations of: unchelated magnesium ions; and of an oxygen scavenger. In embodiments the oxygen scavenger is selected from the group consisting of a pyruvate salt, catalase, a thioglycolate salt, cysteine, Oxyrase™, Na2S, and FeS.

In variants of the embodiment the composition comprises a concentrated mixture of a non-magnesium chelating buffer and a biologically effective concentration of one or more of a magnesium salt, a lithium salt, an iron(III) salt, and a pyruvate salt.

In alternative embodiments the composition comprises a biologically effective combination of at least two, three, or four, five components selected from the group consisting of a magnesium salt, a lithium salt, an iron(III) salt, and a pyruvate salt.

In embodiments the composition comprises a selective agent. In embodiments the composition is for culturing Listeria spp. In embodiments the compositions are used for culturing bacteria which may be Listeria spp.

Kits According to Embodiments

In further series of embodiments there are disclosed kits for culturing bacteria and in embodiments such bacteria are Listeria spp. In embodiments the kit comprises a substantially non-magnesium chelating buffer and; and an oxygen scavenger. In embodiments the oxygen scavenger is selected from the group consisting of a pyruvate salt, catalase, a thioglycolate salt, cysteine, Oxyrase™, Na2S, and FeS.

In embodiments a kit comprises one, two, three or four components selected from the group consisting of a lithium salt, an iron (III) salt, a pyruvate salt, a magnesium salt and non-magnesium chelating buffer. In alternative embodiments the kit also comprises a selective agent and in further embodiments comprises instructions as to how to use the kit to culture the bacteria or how to preferentially culture the bacteria.

In embodiments, the media and methods according to embodiments are or may be suitable to replace the double enrichment steps used in common protocols for the isolation and identification of bacteria, which may be Listeria spp, with a single step enrichment. In embodiments the medium allows or may allo necessary enrichment time for detection of a bacterium to be reduced to about 24 h or less and in embodiments may allow the enrichment time to be less than about 30, 29, 28, 27, 26, 25, 24, 23, 22, 21, 20, 19, 18, 17, 16, 15 hours. In embodiments a single round of culturing is sufficient to reach the sensitivity required for most current technologies, which may be able to detect bacteria at levels of between about $10^3$ to $10^4$ cfu/ml in about 21 hours, 22 hours, 23 hours, or 24 hours of incubation. In embodiments it is possible to achieve these results even with a weak initial inoculum.

Examples

The following examples of embodiments are presented by way of illustration and not limitation.

In one example there is described broth and its use to culture *Listeria* spp.

TABLE 6

Shows the composition of *Listeria* culture medium according to an example of an embodiment

| Ingredients | Manufacturers | Quantity (g/L) |
|---|---|---|
| Phytone | BD BBL (211906) | 5 |
| Tryptone | Oxoid (LP0042) | 5 |
| Beef extract | BD BBL (212303) | 5 |
| Yeast extract | BD Bacto (212750) | 5 |
| Mops-sodium salt | Sigma (M9381) | 13.7 |
| Mops-free acid | Sigma (M1254) | 8.5 |
| Ferric citrate III | Sigma (F6129) | 0.5 |
| Lithium chloride | Sigma (L4408) | 8 |
| $M_gSO_4$ | BDH (BDH0246) | 2 |
| Sodium pyruyate | Sigma (15990) | 1 |
| Selective enrichment supplement* comprising: | Oxoid (SR0141E) | 2.7 mL |
| Cycloheximide | 66-81-9 | 33.75 mg |
| Nalidixic acid | 3374-05-8 | 27 mg |
| Acriflavine hydrochloride | 8048-52-0 | 10.125 mg |

*Reconstitute one vial as directed, and add 2.7 mL of the contents to 1 L of *Listeria* medium.

Sterilize the enrichment broth base with the supplement by autoclaving at 110° C. for 15 minutes.

In a further series of examples there is disclosed medium, its preparation and its use.

Reagents: Actero *Listeria* Enrichment Media.—Specifically optimized medium for the growth and the recuperation of *Listeria* spp. in a single-step enrichment. According to the example the medium is provided in two formats: a bottle of 500 g and a pack of 20 individual pouches of 4.9 g of powder each one.

Additional Supplies and Reagents: Distilled/deionized, sterile water. Any source; Dey-Engley (D/E) neutralizing broth (Lab M Limited, Lancashire, UK) is used for testing of disinfectants and sanitation efficiency; Modified Oxford agar (MOX; Difco Becton Dickinson, N.J., USA); Rapid'L.mono agar (RLM; Bio-Rad, Missisauga, Ontario, Canada) is a chromogenic medium for detection, enumeration, and differentiation of *Listeria* spp., specifically *L. monocytogenes* from food and environmental samples; Biochemical test panel *Listeria* API® system (Biomérieux, Marcy-L'etoile, France); Non-bactericidal 8×4×0.3 cm sterile cellulose sampling sponges pre-moistened with D/E; Filtered sterile stomacher bags; Polypropylene tubes with cap. Available from multiple sources; Disposable transfer pipettes. Any source; Plastic inoculating needles and 10 µL calibrated loops. Any source.

Apparatus: Stomacher Seward 400 Circulator (Seward, London, England).—For thorough mixing of sponge environmental samples in enrichment broth; Micropipet and sterile disposable tips; Stationary incubator Symphony™ (VWR, USA) or equivalent.—To provide 29° C.±0.5° C.; Stationary incubator, model 1555 (VWR, USA) or equivalent.—To provide 35° C.±2° C.

General Preparation of media: To prepare the Actero *Listeria*, suspend 53.8 g of the powder in one liter of distilled water. Heat the mix at 100° C. and stir constantly until complete dissolution of the powder (approx. 35 min). Dispense into final containers and sterilize by autoclaving at 110° C. for 15 min. It is not necessary to autoclave the medium if it is used immediately after preparation. The use of sterile water is recommended in this case.

Sample Preparation: To prepare environmental sponge samples, swab environmental surface of 100 cm² using non-bactericidal cellulose sampling sponges pre-moistened with neutralizing D/E broth approximately 5 vertical and 5 horizontal times (up and down or side to side is considered one time). Place each sponge in a sterile sample bag and keep at 4° C.±2° C. until testing.

Analysis: Add 90 ml of Actero *Listeria* pre-warmed at 29±0.5° C. to each bagged single sponge sample, stomach 30 sec and enrich at 29±0.5° C. for 24 h. Hand mixing is an acceptable alternative for stomaching. To hand mix, massage each sponge for approximately one minute. At the end of the enrichment period, streak the samples directly in MOX and/or in RLM agar plates. Confirm the presumptive *Listeria* spp. colonies as recommended by MLG 8.07 (12) or send them to the independent laboratory for confirmation.

Interpretation and Result Report: If no suspect colonies with morphology typical for *Listeria* spp. have been found on MOX and/or RPM agar plates after 48±2 h of total incubation, the sample is considered negative for *Listeria* spp. If the suspect colonies with morphology typical for *Listeria* spp. have been found on MOX and/or RPM agar plates after 48±2 h of total incubation, the sample should be considered as potentially positive. The suspect colonies must be confirmed according to the USDA FSIS Microbiology Laboratory Guidebook Chapter 8.07, the content of which is incorporated herein in its entirety where permissible by law.

Other Supplies, Reagents and Apparatus Used in This Study: Horse blood overlay agar plates (HBO or HL agar; Quélab Inc., Quebec, Canada); Lactobacilli M.R.S. Broth (MRS; Quélab Inc., Quebec, Canada); Modified University of Vermont broth (UVM; Quélab Inc. Quebec, Canada)—is used for the selective isolation and enrichment of *L. monocytogenes*; Morpholinepropanesulfonic acid-buffered *Listeria* enrichment broth (MOPS-BLEB; Oxoid LTD, Ontario, Canada); Trypticase Soy agar (TSA, Quélab Inc., Quebec Canada) with 0.6% yeast extract (TSA-YE; Bacto™ Yeast Extract; BD Diagnostics, New Jersey, USA); Trypticase Soy agar plates with 5% of sheep blood (blood agar; BBL™ Stacker™, provided by BD Diagnostics, New Jersey, USA); Trypticase Soy Broth (TSB; Quélab Inc., Quebec, Canada) with 0.6% yeast extract (TSB-YE; Bacto™ Yeast Extract, BD Diagnostics, New Jersey, USA); tomacher Seward Circulator 3500 (Seward, London, England).—For thorough mixing of sponge environmental samples in enrichment broth; Vortex mixer (VWR, USA).

Internal Validation Studies: The following validation studies were conducted in the laboratories of Maxivet Inc., a subsidiary company of FoodChek Systems Inc.

Robustness Testing: The ruggedness study was carried out to evaluate the effects of perturbations in two method parameters (the incubation temperature and time), which can affect the performance of the Actero *Listeria*. The ruggedness variables and their respective ranges are shown in Table 1.

Methodology: Each test range condition was evaluated using pure cultures. One target strain, *L. monocytogenes* HPB 5949, and one non-target strain, *E. faecalis* ATCC 19433, were tested.

*L. monocytogenes* HPB 5949 was streaked on blood agar plates and incubated overnight at 35° C.±1° C. A few colonies of the target strain were transferred to 9 mL of TSB-YE for 6-7 h: at 35° C. The culture was diluted 1:10 in fresh TSB-YE and was incubated overnight at the same temperature. Then the culture was diluted to obtain a fractional inoculation level (<1 CFU per sample) in the ALEM broth.

For the non-target strain the same methodology was used for culturing except that the level of inoculation was approximately 10 times more concentrated than the target organism.

Ten (10) replicates of the target and 5 replicates of the non-target bacterium were tested at each parameter.

At the end of the enrichment period, the samples were streaked on MOX and RLM agar plates to confirm the *Listeria* growth.

Results: According to the POD analysis no significant differences were observed between each analyzed parameters since the confidence intervals between the dPOD values of extreme conditions contain a zero (Table 7). So the ability of the Actero Media to recover *L. monocytogenes* HPB 5949 was not affected throughout the temperature and timing ranges tested.

Presence of non-target strain *E. faecalis* ATCC 19433 in the ALEM samples was not detected in any case (data not shown).

TABLE 7

ALEM method robustness results

| Standard parameter | Condition A | Condition B | N[a] | x[b] | Condition A POD (A)[c] | 95% CI | x | Condition B POD (B)[d] | 95% CI | dPOD (AB)[e] | 95% CI[f] |
|---|---|---|---|---|---|---|---|---|---|---|---|
| Incubation temperature (29° C.) | 22 h | 28 h | 10 | 4 | 0.4 | (0.168, 0.687) | 6 | 0.6 | (0.313, 0.814) | −0.2 | (−0.528, 0.206) |
| Incubation time (24 h) | 28° C. | 30° C. | 10 | 3 | 0.3 | (0.108, 0.603) | 4 | 0.4 | (0.168, 0.687) | −0.1 | (−0.446, 0.282) |

[a]N—number of test portions;
[b]x—number of positive test portions;
[c]POD(A)— condition A positive outcomes divided by the total number of trials;
[d]POD(B)—condition B positive outcomes divided by the total number of trials:
[e]dPOD(AB)—difference between condition A and condition B POD values;
[f]95% CI—95% confidence interval (if the 95% CI of a dPOD value does not contain zero, then the difference is statistically significant at the 5% level).

Inclusivity: To test the capacity of the Actero *Listeria* to enrich a variety of *Listeria* spp., 54 strains (Table 8), representing 6 species of *Listeria* genus with an emphasis on the human pathogen *L. monocytogenes* (33 isolates belonging to the 8 most prevalent serotypes), were analyzed.

Methodology: All *Listeria* strains were streaked on blood agar plates and incubated overnight at 35° C. A few colonies were transferred to 10 mL of TSB-YE for 6-7 hours at 35° C. Each culture was diluted 1:10 in fresh TSB-YE and incubated overnight at the same temperature. The culture was then diluted to inoculate approximately 5-20 CFU of each, strain in 10 mL of the ALEM broth. Each strain was incubated in triplicate at 29° C. for 24 h. At the end of the enrichment period, the samples were streaked on MOX and RLM agar plates to confirm the *Listeria* growth.

Results: The results from inclusivity study are summarized in Table 7. All 54 tested *Listeria* strains were able to grow in 24 h at 29° C. using ALEM.

TABLE 8

*Listeria* isolates list—Inclusivity study results

| # | Genus and species | Strain number | Sero-type | Source[a] | Origin | Result |
|---|---|---|---|---|---|---|
| 1 | Listeria grayi | HPB 1114 | — | Health Canada | Non data available | + |
| 2 | Listeria grayi | B-33023 (ATCC19120) | — | ARS | Chinchilla faeces | + |
| 3 | Listeria grayi | B-33018 (ATCC25401) | — | ARS | Standing corn | + |
| 4 | Listeria grayi | ATCC 700545 | — | ATCC | No data available | + |
| 5 | Listeria innocua | HPB 118 | | Health Canada | Food | + |
| 6 | Listeria innocua | HPB 34 | — | Health Canada | Non available data | + |
| 7 | Listeria innocua | B-33314 (OB10387) | — | ARS | Turkey/ham/cheese deli sticks | + |
| 8 | Listeria innocua | MAX-L-3 | | IRDA | Field isolate | + |
| 9 | Listeria innocua | 512 | — | CRDA | No data available | + |
| 10 | Listeria ivanovii | MAX-L-6 | — | IRDA | Field isolate | + |
| 11 | Listeria ivanovii | ATCC 19119 | — | ATCC | Sheep | + |
| 12 | Listeria ivanovii | ATCC BAA-139 | — | ATCC | Washing water | + |
| 13 | Listeria monocytogenes | ATCC 43256 | 1/2b | ATCC | Mexican-style cheese | + |
| 14 | Listeria monocytogenes | MAX-PT-O-2 | 1/2a | IRDA | Manure (soil) | + |
| 15 | Listeria monocytogenes | 513 | 4b | CRDA | No data available | + |
| 16 | Listeria monocytogenes | 514 | 4b | CRDA | No data available | + |
| 17 | Listeria monocytogenes | 515 | 4b | CRDA | No data available | + |
| 18 | Listeria monocytogenes | 516 | 1/2a | CRDA | No data available | + |
| 19 | Listeria monocytogenes | 517 | 4b | CRDA | No data available | + |
| 20 | Listeria monocytogenes | HPB 5255 | 1/2a | Health Canada | Beef—manure pit | + |
| 21 | Listeria monocytogenes | HPB 5916 | 1/2b | Health Canada | Food—lettuce | + |
| 22 | Listeria monocytogenes | HPB 5904 | 1/2a | Health Canada | Food—lettuce | + |
| 23 | Listeria monocytogenes | HPB 5254 | 1/2b | Health Canada | Beef—fresh pen Manure | + |
| 24 | Listeria monocytogenes | HPB 5089 | 1/2c | Health Canada | Food—meat | + |
| 25 | Listeria monocytogenes | HPB 5949 | 1/2c | Health Canada | Food—ready-to-eat Meat | + |
| 26 | Listeria monocytogenes | HPB 5668 | 3a | Health Canada | Food | + |
| 27 | Listeria monocytogenes | HPB 4141 | 3b | Health Canada | Food—raw turkey | + |
| 28 | Listeria monocytogenes | HPB 3 | 4b | Health Canada | Food—milk | + |
| 29 | Listeria monocytogenes | HPB 5246 | 4c | Health Canada | Beef—manure pit | + |
| 30 | Listeria monocytogenes | SHT-2010-00482 | 1/2a | LEPAQ | Goat | + |
| 31 | Listeria monocytogenes | STF-2010-02440 | 4b | LEPAQ | Sheep's head | + |
| 32 | Listeria monocytogenes | SHT-2010-00483 | 1/2a | LEPAQ | Goat | + |
| 33 | Listeria monocytogenes | SHT-2010-00159 | 1/2a | LEPAQ | Goat | + |
| 34 | Listeria monocytogenes | STF-2010-03562 | 1/2a | LEPAQ | Milk | + |

TABLE 8-continued

Listeria isolates list—Inclusivity study results

| # | Genus and species | Strain number | Serotype | Source[a] | Origin | Result |
|---|---|---|---|---|---|---|
| 35 | Listeria monocytogenes | STF-2010-03540 | 1/2b | LEPAQ | Milk | + |
| 36 | Listeria monocytogenes | SHT-2009-01007 | 1/2a | LEPAQ | Goat | + |
| 37 | Listeria monocytogenes | SHY-2010-03610 | 1/2a | LEPAQ | Fresh tissue: liver and kidney | + |
| 38 | Listeria monocytogenes | SHY-2010-00373 | 1/2a | LEPAQ | Milk | + |
| 39 | Listeria monocytogenes | SHT-2010-00055 | 1/2a | LEPAQ | Goat | + |
| 40 | Listeria monocytogenes | STF-2010-00989 | 1/2a | LEPAQ | Milk | + |
| 41 | Listeria monocytogenes | SHT-2010-00122 | 1/2a | LEPAQ | Goat | + |
| 42 | Listeria monocytogenes | SHT-2010-00150 | 1/2a | LEPAQ | Goat | + |
| 43 | Listeria monocytogenes | STF-2011-00729 | 1/2a | LEPAQ | Milk | + |
| 44 | Listeria monocytogenes | SHT-2011-00011 | 1/2a | MAPAQ-FMV | Alive sheep | + |
| 45 | Listeria monocytogenes | STF-2010-06277-1 | 1/2a | LEPAQ | Dead goat | + |
| 46 | Listeria seeligeri | MAX-L-4 | — | IRDA | Field isolate | + |
| 47 | Listeria seeligeri | MAX-PT-LAI-3 | — | IRDA | Field isolate | + |
| 48 | Listeria seeligeri | HPB 3522 | — | Health Canada | Environmental—field water | + |
| 49 | Listeria seeligeri | HPB 272 | — | Health Canada | Animal—raw milk | + |
| 50 | Listeria seeligeri | ATCC 35967 | — | ATCC | Soil | +/− |
| 51 | Listeria welshimeri | HPB 5864 | — | Health Canada | Food—chicken drip | + |
| 52 | Listeria welshimeri | HPB 1137 | — | Health Canada | Food—chicken drip | + |
| 53 | Listeria welshimeri | B-33020 (ATCC35897) | — | ARS | Decaying vegetation | + |
| 54 | Listeria welshimeri | B-33328 (OB20088) | — | ARS | Pork barbecue with sauce | + |

[a]ATCC: American Type Culture Collection, Manassas (VA), United States. IRDA: Research and Development Institute for the Agri-Environment, Quebec (QC), Canada. CRDA: Food Research and Development Center, St-Hyacinthe (QC), Canada. LEPAQ: Laboratory of Expertise in Animal Pathology of Quebec, Quebec (QC), Canada. ARS: Agricultural Research Service, Washington (DC), United States. MAPAQ: Ministry of Agriculture, Fisheries and Food of Quebec, Quebec (QC), Canada. FMV: Laboratory of Bacteriology, Diagnostic Service, Faculty of Veterinary Medicine, St-Hyacinthe (QC), Canada.
+ Presence of typical colonies of Listeria spp.
+/− Presence of typical colonies of Listeria spp. on MOX and/or RLM was observed only when the inoculum was higher than 50 CFU/10 mL of the medium.

Exclusivity: Thirty (30) non-Listeria strains listed in Table 9 were analyzed to determine the ability of the Actero Listeria to discriminate target microorganisms from non-target microorganisms. The strains, belonging to 19 different genera of bacteria and yeasts, were chosen because they are closely related to Listeria spp. or because they are found in the same environment.

Methodology: Each non-Listeria strain was streaked on blood agar plates and incubated overnight at 35° C., and then they were cultured in their optimal conditions as indicated in Table 9. Each suspension was diluted to inoculated 10 mL of the ALEM with a concentration 10 times higher than that used for the target microorganisms. This step was done in triplicate. The culture was grown at 29° C. for 24 h. At the end of the enrichment period, the samples were streaked on MOX and RLM agar plates to verify their ability to grow in the ALEM.

Results: The results obtained from the exclusivity study are summarized in Table 9. No one of the tested strains reported a positive result after enrichment in ALEM at the conditions tested.

TABLE 9

Non-Listeria isolates list - Exclusivity study results

| # | Microorganism | Strain number | Source[a] | Origin | Result |
|---|---|---|---|---|---|
| 1 | Alcaligenes faecalis | ATCC 8750 | FMV | No data available | No growth |
| 2 | Bacillus cereus | ATCC 14579 | FMV | No data available | No growth |
| 3 | Bacillus subtilis | MAX-B-1 | Maxivct Inc. | Manure | No growth |
| 4 | Campylobacter jejuni[e] | — | | No data available | Field isolate | No growth |
| 5 | Candida albicans | ATCC 24433 | FMV | Nail infection | No growth |
| 6 | Carnobacterium divergens | ATCC 35677 | ARS | Vacuum-packed minced beef | No growth |
| 7 | Carnobacterium mobile | ATCC 49516 | ARS | Irradiated chicken meat | No growth |
| 8 | Enterobacter aerogenes | ATCC 13048 | FMV | Sputum | No growth |
| 9 | Enterobacter cloacae | ATCC 23355 | FMV | No data available | No growth |
| 10 | Enterococcus faecalis | ATCC 19433 | FMV | No data available | No growth |
| 11 | Enterococcus faecium | ATCC 8459 | ARS | Dairy products (cheese) | No growth |
| 12 | Escherichia coli | ATCC 25922 | FMV | Clinical isolate | No growth |
| 13 | Hafnia alvei | ATCC 13337 | FMV | Stuart's type 32011 | No growth |
| 14 | Kocuria rhizophila | ATCC 9341 | FMV | Soil | No growth |
| 15 | Lactobacillus acidophilus* | ATCC 314 | FMV | No data available | No growth |
| 16 | Lactobacillus casei* | ATCC 393 | ARS | Dairy products (cheese) | No growth |
| 17 | Lactobacillus plantarum* | ATCC 14917 | ARS | Pickled cabbage | No growth |
| 18 | Lactococcus lactis*[e] | ATCC 7963 | ARS | No data available | No growth |
| 19 | Leuconostoc mesenteroides | ATCC 8086 | ARS | Fermenting string beans | No growth |
| 20 | Proteus mirabilis | ATCC 29906 | No data available | No data available | No growth |
| 21 | Pseudomonas aeroginosa | MSR-0132 | FMV | Soil | No growth |

TABLE 9-continued

Non-*Listeria* isolates list - Exclusivity study results

| # | Microorganism | Strain number | Source[a] | Origin | Result |
|---|---|---|---|---|---|
| 22 | *Pseudomonas fluorescens* | — | FMV | No data available | No growth |
| 23 | *Pseudomonas putida* | — | Maxivet Inc. | No data available | No growth |
| 24 | *Rhodococcus equi*\* | ATCC 6939 | FMV | Lung abscess of foal | No growth |
| 25 | *Salmonella typhimurium* | ATCC 14028 | No data available | Tissue, animal | No growth |
| 26 | *Staphylococcus aureus* | ATCC 25923 | FMV | Clinical isolate | No growth |
| 27 | *Staphylococcus epidermidis* | — | MAPAQ | No data available | No growth |
| 28 | *Staphylococcus saprophyticus* | — | FMV | Mastitis | No growth |
| 29 | *Staphylococcus xylosus* | — | FMV | Mastitis | No growth |
| 30 | *Streptococcus agalactiae* | ATCC 13812 | FMV | No data available | No growth |

[a]ARS: Agricultural Research Service, Washington (DC), United States. FMV: Laboratory of Bacteriology, Diagnostic Service, Faculty of Veterinary Medicine, St-Hyacinthe (QC), Canada. MAPAQ: Ministry of Agriculture, Fisheries and Food of Quebec, Quebec (QC), Canada.
\*48 h of incubation in MRS broth.
\*\*48 h of incubation in TSB.
*5% $CO_2$.

Lot-to-Lot Testing: The objective of this study is to ensure that the manufacturing is consistent between lots of the medium.

Methodology: Three independent lots were used to confirm the manufacturing reproducibility of the ALEM. Each lot was evaluated using one target strain, *L. monocytogenes* HPB 5949, and one non-target strain, *E. faecalis* ATCC 19433.

The target strain was streaked on blood agar plates and incubated overnight at 35° C. A few colonies were transferred to 9 mL of TSB-YE for 6-7 h at 35° C. The bacterial culture was diluted 1:10 in fresh TSB-YE and incubated overnight at the same temperature. The culture was then diluted to obtain a fractional inoculum (approximately 0.5 CFU per sample) into 10 mL of the ALEM broth.

For the non-target strain, the same methodology was used for culturing except that the level of inoculation was approximately 5 CFU (10 times more concentrated than the target organism). Ten (10) replicates of the target and 5 replicates of the non-target bacterium were tested. The cultures were grown at 29° C. for 24 h. At the end of the enrichment period, the samples were streaked on MOX and RLM agar plates for confirmation.

Results: A successful performance test was carried out with three different batches of the Actero *Listeria*. The stability in the manufacturing process was proved by the POD analysis with a confidence interval of 95% (please see Table 10).

Methodology: The Actero *Listeria* was evaluated at each proposed storage time point using one target strain, *L. monocytogenes* HPB 5949, and one non-target strain, *E. faecalis* ATCC 19433. The target strain was streaked on blood agar plates and incubated overnight at 35° C. A few colonies were transferred to 9 mL of TSB-YE for 6-7 h at 35° C. The culture was diluted 1:10 in fresh TSB-YE and incubated overnight at the same temperature. Then the culture of the target bacterium was diluted to obtain a fractional inoculum (0.5 CFU per sample) into 10 mL of the ALEM broth. For the non-target strain, the same methodology was used for culturing except that the level of inoculation was approximately 5 CFU (10 times more concentrated than the target organism). Ten (10) replicates of the target and 5 replicates of the non-target bacterium were tested. The cultures were grown at 29° C. for 24 h. At the end of the enrichment, period, the samples were streaked on MOX and RLM agar plates for confirmation.

Results: The results of the stability study are reported in Table 11. Confidence intervals between the dPOD values of two extreme storage time points of the prepared ALEM contain a zero confirming an absence of significant changes in the media performance after 45 days of storage as compared to the freshly prepared media. No significant differences were also determined between other different storage time points of the prepared ALEM (data not shown). These data indicate that the prepared ALEM can be stored at 4° C. without any significant changes in the performance values during 45 days after preparation.

TABLE 10

ALEM lot-to-lot testing results

| Level of Inoculum, CFU/sample | $N^a$ | $x^b$ | Lot 1 | | Lot 2 | | | Lot 3 | | | |
|---|---|---|---|---|---|---|---|---|---|---|---|
| | | | POD $(A)^c$ | 95% CI | x | POD $(B)^d$ | 95% CI | x | $POD_c^e$ | 95% CI | dPOD $(CB)^f$ | 95% $CI^g$ |
| 0.7 | 10 | 3 | 0.3 | (0.108, 0.603) | 4 | 0.4 | (0.168, 0.687) | 2 | 0.2 | (0.057, 0.510) | −0.2 | (−0.521, 0.187) |

[a]N—number of test portions;
[b]x—number of positive test portions;
[c]POD(A)—lot 1 positive outcomes divided by the total number of trials;
[d]POD(B)—lot 2 positive outcomes divided by the total number of trials;
[e]POD(C)—lot 3 positive outcomes divided by the total number of trials;
[f]dPOD(CB)—difference between extreme POD values (lot 3 POD values and lot 2 POD values);
[g]95% CI—95% confidence interval (if the 95% CI of a dPOD value does not contain zero, then the difference is statistically significant at the 5% level).

Stability Testing: The stability of the prepared ALEM was examined over a storage period of 6 weeks at 4° C. in a dark place. The performance of the ALEM was tested at 0 (freshly prepared), 2, 4 and 6 weeks of storage using a target and non-target bacteria.

Matrix Study: The matrix study was performed to evaluate the ability of ALEM broth to recover the *Listeria* spp. from stainless steel in one enrichment step.

The isolates used for these studies are field isolates originating from food and well characterized by a research laboratory of Health Canada. *Listeria monocytogenes* strain HPB 5949 and *L. innocua* strain HPB 118 will be used to validate the test with stainless steel and plastic surfaces respectively.

The study using the stainless steel plates was carried out at Maxivet Inc. and the other using plastic surfaces was executed in collaboration with an external laboratory (please see the section "Independent Validation Study").

below. The remaining sponge samples were analyzed using the reference method MLG 8.07.

ALEM enrichment procedure: One set of the sponge samples (20 inoculated and 5 non-inoculated) was treated as follow: 90 mL of ALEM pre-warmed at 29±0.5 C were added to each bagged single sponge sample. The samples were stomached 30 sec and enriched at 29±0.5° C. for 24 h. At the

TABLE 11

ALEM stability testing results

| | | | Prepared ALEM Storage Time, day | | | | | | | | | | | | | |
|---|---|---|---|---|---|---|---|---|---|---|---|---|---|---|---|---|
| | | | 0 | | | 14 | | | 30 | | | 45 | | | | |
| $N^a$ | $I^b$ | $x^c$ | POD $(A)^d$ | 95% CI | I | x | POD $(B)^e$ | 95% CI | I | x | POD $(C)^f$ | 95% CI | I | x | POD $(D)^g$ | 95% CI | CI$^j$ |
| 10 | 0.7 | 3 | 0.3 | (0.108, 0.603) | 0.5 | 3 | 0.3 | (0.108, 0.603) | 0.5 | 4 | 0.4 | (0.168, 0.687) | 0.2 | 2 | 0.2 | (0.057, 0.510) | (−0.435, 0.265) |

$^a$N—number of test portions;
$^b$I—level of the inoculum, CFU/portion;
$^c$x—number of positive test portions;
$^d$POD(A)—fresh prepared ALEM positive outcomes divided by the total number of trials;
$^e$POD(B)—14 days stored ALEM positive outcomes divided by the total number of trials;
$^f$POD(C)—30 days stored ALEM positive outcomes divided by the total number of trials;
$^g$POD(D)—45 days stored ALEM positive outcomes divided by the total number of trials;
$^j$95% CI—95% confidence interval (if the 95% CI of a dPOD value does not contain zero, then the difference is statistically significant at the 5% level).
The dPOD(AD) for the results presented is −0.1, representing the difference between POD values of extreme storage time points of the prepared medium (0 and 45 days) as well as between POD values of extreme inoculum levels (0.2 and 0.7 CFU/portion):

Methodology: Inoculum preparation: *L. monocytogenes* HPB 5949 used as a target strain and *E. faecalis* ATCC 19433 used as a competitor were streaked on blood agar plates and incubated overnight at 35° C. A few colonies will be transferred to 10 mL of TSB-YE for 6-7 h at 35° C. The cultures were diluted 1:10 in fresh TSB-YE and incubated overnight at the same temperature. After incubation, the cultures were stored at 4±2° C. until use.

A mix of target strain and non-target strain (ratio 1:10) was used as inoculum for stainless steel plates. The mix was prepared as follow. The *L. monocytogenes* HPB 5949 was diluted in 10% no fat dry milk (NFDM) to obtain fractionary positive results. Furthermore, the *E. faecalis* culture was also diluted in 10% NFDM to obtain a concentration 10 times higher than the target strain. The bacterial cell concentration of each strain was verified by plaiting before mixing them.

Environmental sample preparation: Stainless steel plates of 100 cm² were obtained from a supplier specialized in food industry. Before use, all plates were cleaned and sterilized by autoclaving.

Forty: (40) stainless steel plates were inoculated with 250 μL of the mix culture (prepared as described in Section 6.1.1.) by spreading many drops through the entire surface. Then other 10 stainless steel plates were inoculated with 250 μL of 10% NFDM as negative control.

The surfaces were dried for 18-20 h inside a closed Laminar Flow Biological Safety Cabinet at room temperature (22±2° C.). Each plate was swabbed using non-bactericidal cellulose sampling sponge (Nasco Whirl-Pak Speci-Sponge, Nasco, USA) pre-moistened with neutralizing D/E broth approximately 5 vertical and 5 horizontal times (up and down or side to side is considered one time). Each sponge was placed in a sterile sample bag and keep at room temperature for at least 2 h.

Half of the sponge samples from swabbed inoculated and non-inoculated stainless steel plates were analyzed using the method developer protocol (ALEM protocol) described end of the enrichment period, the samples were directly streaked on MOX and RLM agar plates using a calibrated loop of 10 μL.

The presumptive *L. monocytogenes* colonies were confirmed by rapid biochemical testing using API *Listeria* as recommended by MLG 8.07.

ALEM enrichment confirmation: The results obtained according to the ALEM protocol were confirmed by double enrichment following the USDA-FSIS reference protocol.

For that 0.1±0.02 mL of the ALEM enriched sample was transferred into 10±0.5 mL of MOPS-BLEB and incubated at 35±2.0° C. for 24 h. MOX agar plates were then directly streaked and incubated at 35±2.0° C. for 24-28 h.

Suspected colonies were transferred from MOX agar plates to HL agar and incubated 35±2.0° C. for 18-26 h. Rapid biochemical procedure using API *Listeria* was performed to confirm the presumptive positive isolated colonies as recommended by MLG 8.07.

Reference method enrichment and confirmation: The second set of the sponge samples (20 inoculated and 5 non-inoculated) stomached in 225±5 mL of UVM broth for 2±0.2 min was enriched at 30±2.0° C. for 22±2 h. After that 0.1±0.02 mL of the UVM enriched sample was transferred to 10±0.5 ml of MOPS-BLEB and incubated at 35±2.0° C. for 18-24±2 h.

At the end of the each enrichment period, the samples were directly streaked on MOX agar plates. All presumptive positive samples were confirmed by the rapid biochemical procedure using API *Listeria* performed according to the MLG 8.07.

Results: Results from the ALEM matrix study are presented in Table 12. Fifteen (15) of 20 samples inoculated and treated according to the developer method protocol were confirmed as positives. In contrast, only 5 positive outcomes were observed among 20 inoculated samples which have been processed using the reference method protocol. No false negatives were found in all tested samples.

TABLE 12

Comparative results for the detection of *L. monocytogenes* in stainless steel plate sponge samples

| Statistic | $I^a$, CFU/test sample | Candidate presumptive (CP) | | | Candidate confirmed (CC) | | | Candidate method (C) | | | Reference method (R) | | | C vc R dPOD (C, R)$^g$ | CP vc CC dPOD (CP, CC)$^h$ |
|---|---|---|---|---|---|---|---|---|---|---|---|---|---|---|---|
| | | $N^b$ | $x^c$ | POD(CP)$^d$ | N | x | POD(CC)$^e$ | N | x | POD(C) | N | x | POD(R)$^f$ | | |
| Estimate | 0.00 | 5 | 0 | 0.00 | 5 | 0 | 0.00 | 5 | 0 | 0.00 | 5 | 0 | 0.00 | 0.00 | 0.00 |
| LCL | | | | 0.00 | | | 0.00 | | | 0.00 | | | 0.00 | −0.43 | −0.43 |
| UCL | | | | 0.43 | | | 0.43 | | | 0.43 | | | 0.43 | 0.43 | 0.43 |
| Estimate | 1.50 | 20 | 15 | 0.75 | 20 | 15 | 0.75 | 20 | 15 | 0.75 | 20 | 5 | 0.25 | 0.50 | 0.00 |
| LCL | | | | 0.53 | | | 0.53 | | | 0.53 | | | 0.11 | 0.19 | −0.26 |
| UCL | | | | 0.89 | | | 0.89 | | | 0.89 | | | 0.47 | 0.70 | 0.26 |

$^a$I—level of the inoculum, CFU/sample;
$^b$N—number of test samples;
$^c$x—number of positive test samples;
$^d$POD(CP)—candidate method presumptive positive outcomes divided by the total number of trials;
$^e$POD(CC)—candidate method confirmed positive outcomes divided by the total number of trials;
$^f$POD(R)—confirmed reference method positive outcomes divided by the total number of trials;
$^g$dPOD(C, R)—difference between the candidate method result and reference method result POD values;
$^h$dPOD(CP, CC)—difference between the candidate method presumptive result and the candidate method confirmed result POD values.

Independent Validation Study: Validation study was conducted in collaboration with an external accredited testing laboratory Agat Laboratories (Sant-Laurent, Quebec, Canada) under the AOAC supervision.

Method Comparison: The method comparison study was performed to evaluate the ability of ALEM broth to recover the *Listeria* spp. from plastic plate environmental samples after 24 h of enrichment at 29° C.

Methodology: Inoculum preparation: *L. innocua* MAX-L-3 used as a target strain was streaked on blood agar plates and incubated overnight at 35° C. A few colonies will be transferred to 10 mL of TSB-YE for 6-7 h at 35° C. The culture was diluted 1:10 in fresh TSB-YE and incubated overnight at the same temperature. After incubation, the culture was stored at 4±2° C. until use. The culture was diluted in 10% no fat dry milk (NFDM) to inoculate plastic environmental surface with a low inoculation level in the aim to obtain fractionary positive results. The bacterial cell concentration was verified after inoculation by plaiting.

Sample preparation: Plastic plates of 100 cm$^2$ were obtained from a supplier specialized in food industry. Before use, all plates were cleaned and sterilized by autoclaving.

Forty (40) plastic plates were inoculated with 250 µL of *L. innocua* MAX-L-3 culture (prepared as described in Section 1.1.1.) by spreading many drops through the entire surface. Then other 10 plastic plates were inoculated with 250 µL of 10% NFDM as negative control. The surfaces were dried for 18-20 h inside a closed Laminar Flow Biological Safety Cabinet at room temperature (22±2° C.).

Environmental sponge samples were obtained as follow: each plastic plate was swabbed using non-bactericidal cellulose sampling sponge (Nasco Whirl-Pak Speci-Sponge, Nasco, USA), pre-moistened with neutralizing D/E broth approximately 5 vertical and 5 horizontal times (up and down or side to side is considered one time). Each sponge was placed in a sterile sample bag and keep at room temperature for at least 2 h.

Half of the sponge samples from swabbed inoculated and non-inoculated plastic plates were analyzed using the method developer protocol (ALEM protocol) described below. The remaining sponge samples were analyzed using the reference method MLG 8.07.

ALEM enrichment protocol: One set of the sponge samples (20 inoculated and 5 non-inoculated) was treated as follow: 90 mL of ALEM pre-warmed at 29±0.5° C. were added to each bagged single sponge sample. The samples were stomached 30 sec and enriched at 29±0.5° C. for 24 h. At the end of the enrichment period, the samples were directly streaked on MOX and RLM agar plates. The presumptive *L. innocua* colonies were confirmed by rapid biochemical testing using API *Listeria* as described in MLG 8.07 reference method.

ALEM enrichment confirmation: The results obtained according to the ALEM protocol were confirmed by double Enrichment; as recommended by USDA-FSIS reference protocol.

For that 0.1±0.02 mL of the ALEM enriched sample was transferred into 10±0.5 mL of MOPS-BLEB and incubated at 35±2.0° C. for 24 h. MOX agar plates were then directly streaked and incubated at 35±2.0° C. for 24-28 h.

Suspected colonies were transferred from MOX agar plates to HL agar and incubated at 35±2.0° C. for 18-26 h. Rapid biochemical procedure using API *Listeria* was performed to confirm the presumptive positive isolated colonies as recommended by MLG 8.07 reference method.

Reference method enrichment and confirmation: The second set of the sponge samples (20 inoculated and 5 non-inoculated) was stomached in 225±5 ml of UVM broth for 2±0.2 min and was enriched at 30±2.0° C. for 22±2 h. After that 0.1±0.02 mL of each UVM enriched sample was transferred to 10±0.5 ml of MOPS-BLEB and incubated at 35±2.0° C. for 18-24±2 h.

At the end of the each enrichment period, the samples were directly streaked on MOX agar plates. All presumptive positive samples were confirmed by the rapid biochemical procedure using API *Listeria* according to the MLG 8.07 reference method.

Results: Results from the method comparison study are presented in Table 13. Based on the POD and the Chi-square unpaired analyses, no significant difference was noted between the developer method protocol and the reference method protocol for the recovery of *L. innocua* from plastic food contact surface. No one false negative, outcome or false positive outcome was reported. Table 14 summarises the performance parameters for the Actero *Listeria* method.

TABLE 13

Comparative results for the detection of L. innocua in plastic plate environmental sponge samples

| Statistic | $I^a$, CFU/test sample | Candidate presumptive (CP) | | | Candidate confirmed (CC) | | | Candidate method (C) | | | Reference method (R) | | | C vc R dPOD | CP vc CC dPOD |
|---|---|---|---|---|---|---|---|---|---|---|---|---|---|---|---|
| | | $N^b$ | $x^c$ | POD(CP) | N | x | POD(CC) | N | x | POD(C) | N | x | POD(R) | (C, R) | (CP, CC) |
| Estimate | 0.00 | 5 | 0 | 0.00 | 5 | 0 | 0.00 | 5 | 0 | 0.00 | 5 | 0 | 0.00 | 0.00 | 0.00 |
| LCL | | | | 0.00 | | | 0.00 | | | 0.00 | | | 0.00 | −0.43 | −0.43 |
| UCL | | | | 0.43 | | | 0.43 | | | 0.43 | | | 0.43 | 0.43 | 0.43 |
| Estimate | 6.20 | 20 | 7 | 035 | 20 | 7 | 0.35 | 20 | 7 | 0.35 | 20 | 6 | 0.30 | 0.05 | 0.00 |
| LCU | | | | 0.18 | | | 0.18 | | | 0.18 | | | 0.15 | −0.23 | −0.28 |
| UCL | | | | 0.57 | | | 0.57 | | | 0.57 | | | 0.52 | 0.32 | 0.28 |

[a] I—level of the inoculum, CFU/sample;
[b] N—number of test samples;
[c] x—number of positive test samples;
[d] POD(CP)—candidate method presumptive positive outcomes divided by the total number of trials;
[e] POD(CC)—candidate method confirmed positive outcomes divided by the total number of trials;
[f] POD(R)—confirmed reference method positive outcomes divided by the total number of trials;
[g] dPOD(CP)—difference between the candidate method result and reference method result POD values;
[h] dPOD(CP)—difference between the candidate method presumptive result and candidate method confirmed result POD values.

TABLE 14

Summary of performance parameters for Actero Listeria Method

| Matrix | Strain | $I^a$, CFU/test sample | $N^b$ | Reference confirmed positive (CP) | Candidate presumptive positive (CP) | Candidate confirmed positive (CC) | Sensitivity, % | Specificity, % | Accuracy, % | Method Agreement, % | $z^{2c}$ |
|---|---|---|---|---|---|---|---|---|---|---|---|
| Stainless steel plate | L. monocytogenes HPB 5949 | 0.00 | 5 | 0 | 0 | 0 | n/a | 100 | n/a | 100 | 9.8 |
| | | 3.2 | 20 | 5 | 15 | 15 | 100 | 100 | 300 | | |
| Plastic plate | L. innocuo MAX-L-3 | 0.00 | 5 | 0 | 0 | 0 | n/a | 100 | n/a | 100 | 0.1 |
| | | 6.20 | 20 | 6 | 7 | 7/6 | 100 | 100 | 117 | | |

[a] I—level of the inoculum, CFU/sample;
[b] N—number of test samples;
[c] $z^2$—defined by Cochran-Mantel-Haenszel impaired analysis ($z^2$ results greater than 3.84 indicate a significant difference between two methods at a 95% confidence level);
n/a—not applicable.

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed. Particular embodiments may alternatively comprise or consist of or exclude any one or more of the elements disclosed.

The embodiments of the invention in which an exclusive property or privilege is claimed are defined as follows:

1. A culture medium for selective growth of Listeria spp., comprising:
   between about 1 g/L and 10 g/L of enzymatically digested soybean meal;
   between about 1 g/L and 10 g/L tryptone;
   between about 1 g/L and 10 g/L beef extract;
   between about 1 g/L and 10 g/L yeast extract;
   between about 10 g/L and 45 g/L of MOPS buffer;
   between about 0.1 g/L and 0.5 g/L of iron (III) citrate;
   between about 7 g/L and 9 g/L of lithium chloride;
   between about 0.6 and 5 g/L of $MgSO_4$;
   between about 1 g/L and 5 g/L of sodium pyruvate; and
   a biologically effective combination of nalidixic acid, cycloheximide and acriflavine hydrochloride.

2. The medium according to claim 1, comprising:
   about 5 g/L of enzymatically digested soybean meal;
   about 5 g/L of tryptone;
   about 5 g/L of beef extract;
   about 5 g/L of yeast extract;
   between about 7.2 g/L and 26 g/L of MOPS Sodium salt;
   between about 4.5 g/L and 16.2 g/L of MOPS free acid;
   about 0.5 g/L of iron (III) citrate;
   about 8 g/L of lithium chloride;
   about 2 g/L of $MgSO_4$;
   about 1 g/L of sodium pyruvate; and
   a biologically effective combination of nalidixic acid, cycloheximide and acriflavine hydrochloride.

3. The medium according to claim 2, wherein said nalidixic acid is present at a concentration of about 27 mg/L, said cycloheximide is present at a concentration of about 34 mg/L, and said acriflavine hydrochloride is present at a concentration of about 10 mg/L.

4. The medium according to claim 2, wherein said cycloheximide is present at a concentration of about 33.75 mg/L, and said acriflavine hydrochloride is present at a concentration of about 10.125 mg/L.

5. A method for selectively culturing Listeria present in a biological sample, the method comprising the step of culturing the sample in a medium according to claim 1.

6. The method according to claim 5, wherein the method do not include a second culturing step.

7. The method according to claim 5, wherein said culturing is carried out at between about 29° C. and 37° C.

8. The method according to claim 7, wherein said culturing is carried out at a temperature between about 28.5° C. and 29.5° C.

9. The method according to claim 5, wherein said culturing lasts 28 hours or less.

10. The method according to claim 5, wherein the biological sample has been frozen, refrigerated, ground, chopped, canned, heat treated, dried, preserved or refined.

11. The method according to claim 5, wherein the *Listeria* comprises a strain selected from the group consisting of *Listeria monocytogenes, Listeria ivanovii, Listeria welshimeri, Listeria seeligeri, Listeria innocua*, and *Listeria grayi*.

12. The method according to claim 5, further comprising, following said culturing step, detecting the presence of *Listeria* in the medium.

13. The method of claim 12, wherein said detecting comprises a PCR, lectin binding, simple diffusion, lateral diffusion, immunological detection, lateral flow, ELISA or flow through step.

14. A kit for detecting *Listeria* spp., the kit comprising (1) the ingredients to manufacture the medium according to claim 1 and (2) instructions to culture said *Listeria* spp. using said medium.

15. The kit according to claim 14, further comprising an apparatus for detecting the *Listeria* spp.

* * * * *